United States Patent [19]

Hagiwara et al.

[11] Patent Number: 5,251,076
[45] Date of Patent: Oct. 5, 1993

[54] RECORDING APPARATUS FOR ELECTROCARDIOGRAPHS

[75] Inventors: Motoharu Hagiwara, Chiba; Kazumasa Sato; Isao Tamaki, both of Tokyo; Tadao Sasaki, Kanagawa; Yasukazu Sato, Tokyo; Yoichi Hishijima; Mitsuru Harada, both of Kanagawa; Hirokazu Kimura, Tokyo, all of Japan

[73] Assignee: Sony Corporation, Tokyo, Japan

[21] Appl. No.: 666,021

[22] Filed: Mar. 7, 1991

[30] Foreign Application Priority Data

Mar. 7, 1990 [JP] Japan .................... 2-55526
Mar. 16, 1990 [JP] Japan .................... 2-66176
Mar. 20, 1990 [JP] Japan .................... 2-69992

[51] Int. Cl.$^5$ ................................. G11B 5/09
[52] U.S. Cl. ........................... 360/32; 360/39
[58] Field of Search ............ 360/32, 39, 46, 51

[56] References Cited

U.S. PATENT DOCUMENTS

| | | | |
|---|---|---|---|
| 4,303,988 | 12/1981 | Tsuboka et al. | 360/32 X |
| 4,328,580 | 5/1982 | Stockham, Jr. et al. | 360/32 |
| 4,528,689 | 7/1985 | Katz | 360/32 X |
| 5,021,893 | 6/1991 | Scheffler | 360/32 X |

Primary Examiner—David Mis
Attorney, Agent, or Firm—Hill, Steadman & Simpson

[57] ABSTRACT

A magnetic recording apparatus for electrocardiographs wherein an input signal is converted into a digital signal, such digital signal is accumulated and intermittently recorded, thereby enabling electric power consumption to be reduced and efficiency of use to be improved. Parallel memories are used to store the digital signal at a first rate and the digital signal is read from the memories at a second rate higher than the first rate.

3 Claims, 10 Drawing Sheets

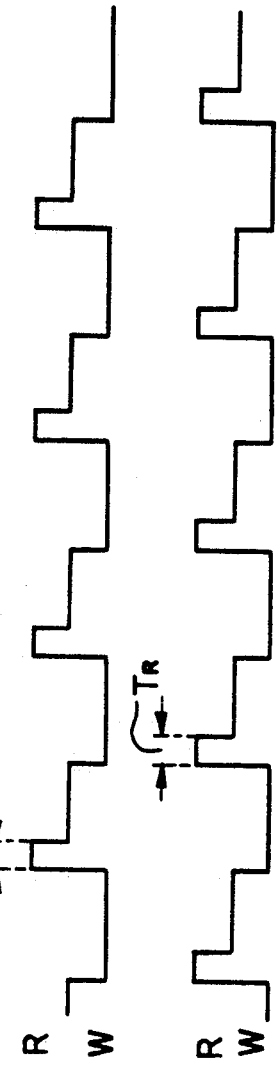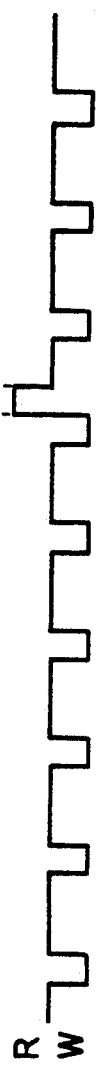
Fig. 2A
Fig. 2B
Fig. 2C
Fig. 2D
Fig. 2E

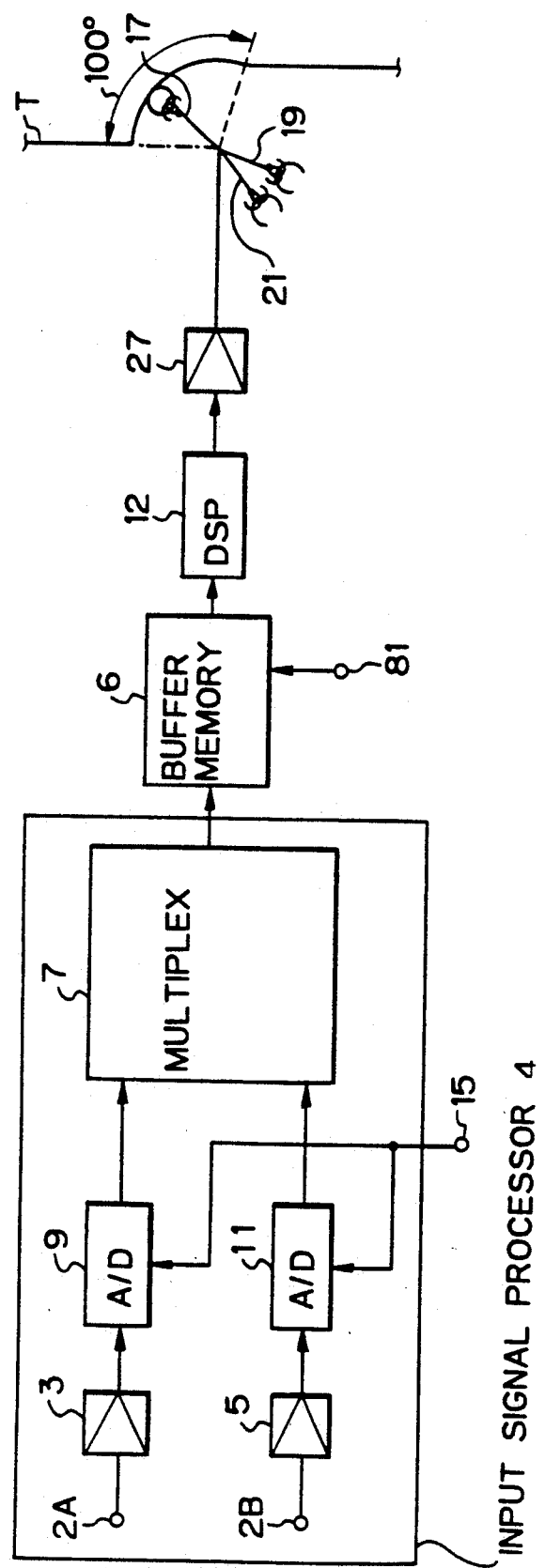

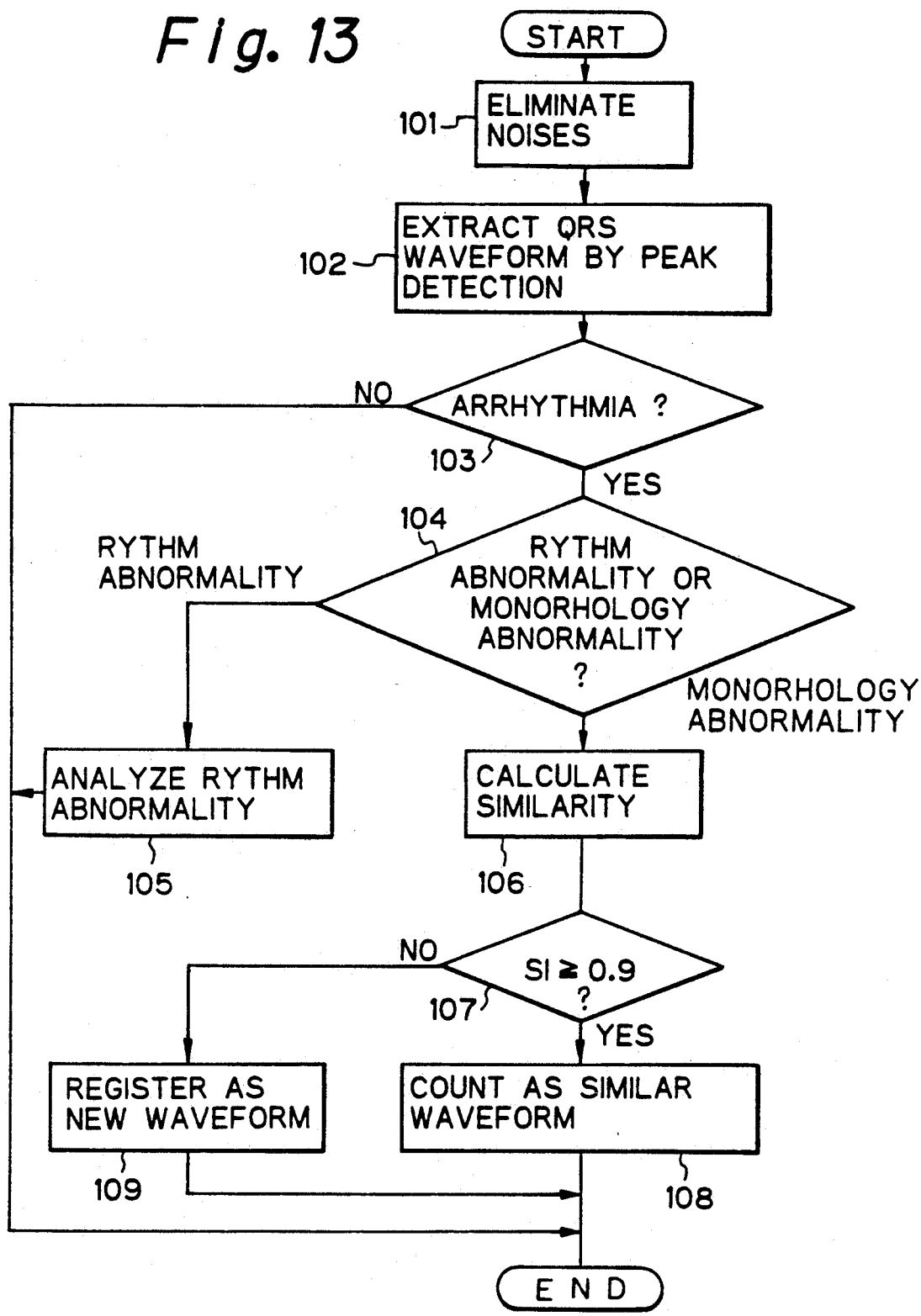

RECORDING APPARATUS FOR ELECTROCARDIOGRAPHS

BACKGROUND OF THE INVENTION

1. Field of the Invention

The present invention relates to a RECORDING APPARATUS FOR ELECTROCARDIOGRAPHS.

2. Description of the Related Background Art

The Holter electrocardiogram method is one technique to collect and analyze electrocardiogram waveforms. According to the Holter electrocardiogram method, electrocardiogram waveforms obtained for a subject and are recorded for a relatively long time, e.g., 24 hours or longer, and then are automatically analyzed by an analyzing system. Since the recording is executed for a long time, a small size and a light weight are also required for a recording apparatus of the electrocardiogram waveforms so that it can be carried out by the subject for a long time. An analog tape recorder is generally used as a conventional recording apparatus of electrocardiograms. Electrocardiogram waveforms are recorded to a compact cassette, a microcassette, or the like at a low speed by the analog tape recorder.

Detection and discrimination of an arrhythmia can be one of the analysis items of the electrocardiogram waveforms. In the diagnosis of an arrhythmia, a morphology abnormality of the electrocardiogram waveform is observed together with a rhythm abnormality of the heartbeat.

However, most of the portion of the electrocardiogram width, the portion of S-T, and the like of the electrocardiogram signal are constructed by signal components of a direct current. Therefore, when the electrocardiogram signal is directly magnetically recorded by running a magnetic tape at an extremely low speed as in the conventional electrocardiogram recording apparatus, the occurrence of a waveform distortion cannot be avoided and it is difficult to accurately record the electrocardiogram signal. Also, because it is necessary to record the electrocardiogram signal for a long time, e.g., about 24 hours, there is a problem in that the size of the battery providing the power inevitably increases and portability of the apparatus deteriorates.

A method whereby an electrocardiogram signal is converted into a digital signal and recorded is considered as one of the methods of accurately recording an electrocardiogram signal (refer to JP-A-1-104247). However, even if the above method is used, electric power consumption cannot be reduced and there is a problem in that the above method is still insufficient as a countermeasure. In JP-A-1-48236, there has been disclosed a method whereby an electrocardiogram waveform is selected, the selected electrocardiogram waveform is converted into the digital signal, electrocardiogram waveforms obtained in a predetermined period of time and displayed by a display section are observed, and when the waveform to be recorded appears, an instruction to start the recording is generated from an operating section, thereby recording the electrocardiogram waveform.

However, in the above conventional technique, many electrocardiogram waveforms must always be observed in order to selectively record only a desired electrocardiogram waveform. With respect to such point, there is a problem in that it is difficult to apply the above technique to the Holter electrocardiogram method. On the other hand, the foregoing morphology abnormality of the electrocardiogram waveform is discriminated by comparing with the normal electrocardiogram waveform and is classified into the morphology. The electrocardiogram waveforms regarding the respective classified morphologies and the appearance frequencies of the electrocardiogram waveforms of the respective morphologies are used together with the foregoing rhythm abnormality of the heartbeat as references for a medical diagnosis. However, there is a problem in that there is no established reference as a method of classifying the morphology of the electrocardiogram waveform.

In JP-A-57-96638, there has been proposed a technique to quantitatively analyze an electrocardiogram waveform by applying an analyzing method called a Lorentz plot to a generation period of electrocardiogram waveforms. However, in the above conventional technique, various analyses are mainly executed by paying attention to the generation period of the electrocardiogram waveforms and there is a problem in that nothing is disclosed with respect to the morphology classification of the electrocardiogram waveform.

OBJECTS AND SUMMARY OF THE INVENTION

It is an object of the invention to provide a magnetic recording apparatus which can record a signal at a high accuracy for a long time while reducing an electric power consumption.

Another object of the invention is to provide a processing method of electrocardiogram waveforms which can classify a morphology of the electrocardiogram waveform on the basis of a clear reference.

According to the invention, in a magnetic recording apparatus, an input signal is converted into a digital signal and accumulated and intermittently recorded, thereby enabling an electric power consumption to be reduced and enabling a using efficiency to be improved.

Further, according to the invention, there is provided a magnetic recording apparatus having memory means for storing a digital signal which is obtained by converting an analog signal, wherein the digital signal is stored into the memory means at a first frequency according to a desired band width of the analog signal, the digital signal is read out at a second frequency higher than the first frequency and is recorded onto a tape-shaped recording medium whose feeding speed is set in accordance with a ratio of the first and second frequencies, so that a recording time can be set to be longer than a conventional recording time in the recording mode and a reproducing time can be less than the time which was required to record in the reproducing mode.

Further, according to the invention, in a processing method of an electrocardiogram waveform which is obtained as mentioned above, by classifying the waveform of the electrocardiogram on the basis of multi dimensional vectors of Nth dimension, the morphology classification of the electrocardiogram waveform can be executed by the clear reference and a classification accuracy can be improved.

The above and other objects and features of the present invention will become apparent from the following detailed description and the appended claims with reference to the accompanying drawings.

BRIEF DESCRIPTION OF THE DRAWINGS

FIGS. 2-2E is a signal waveform diagram to explain the operation of the above apparatus;

FIG. 3 is a block diagram of another embodiment of the invention;

FIG. 13 is a flowchart showing an embodiment of the invention;

DETAILED DESCRIPTION OF THE PREFERRED EMBODIMENT

Figure 1:
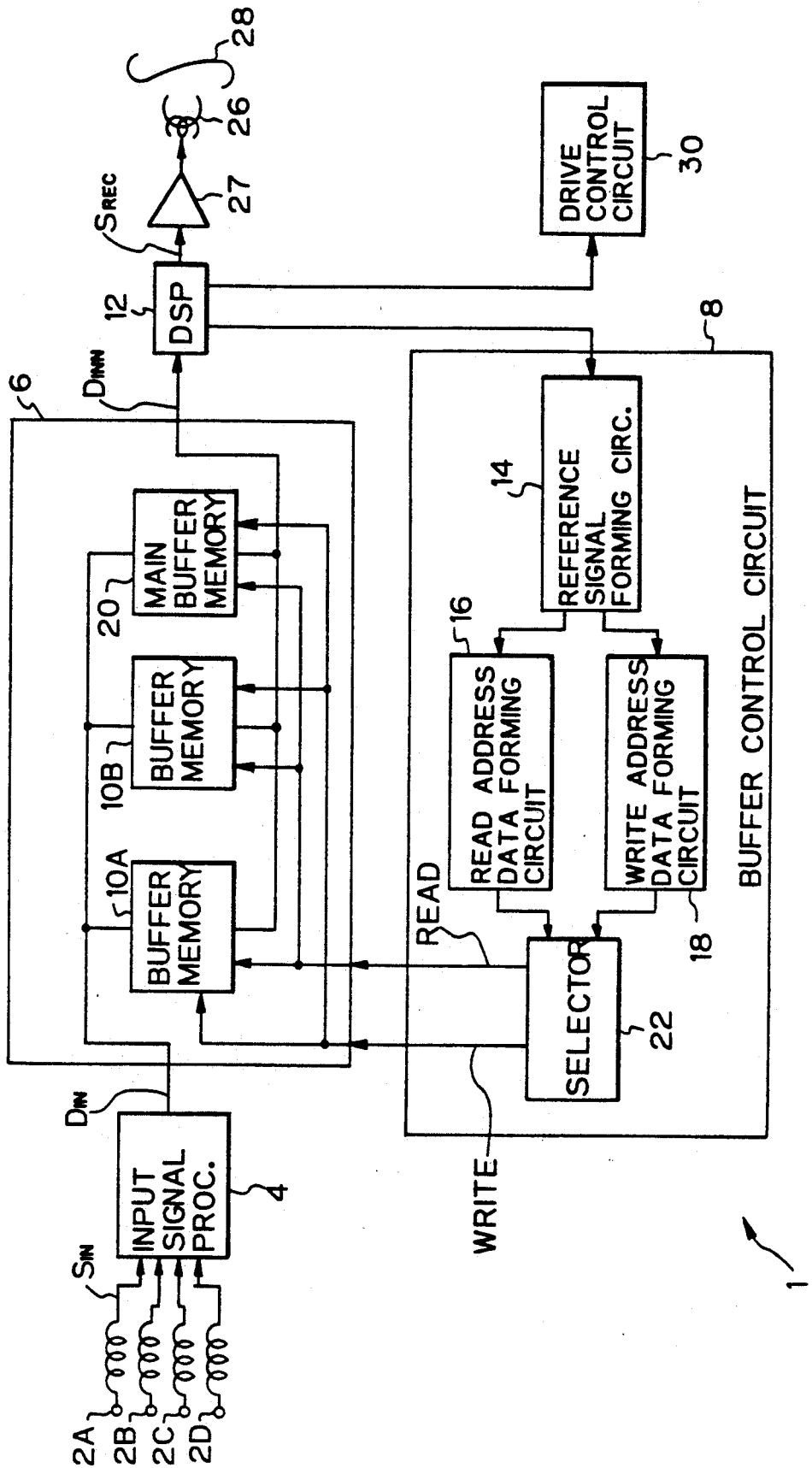
FIG. 1 is a block diagram showing an electrocardiogram recording apparatus according to an embodiment of the invention.

An embodiment of the invention will be described in detail hereinbelow with reference to the drawings. In FIG. 1, reference numeral 1 denotes an electrocardiogram recording apparatus as a whole. Electrocardiogram signals $S_{IN}$ which are generated from four electrodes 2A to 2D, comprising pickup elements, are supplied to an input signal processor 4.

As shown in FIG. 2, the input signal processor 4 converts the electrocardiogram signals $S_{IN}$ ((A) in FIG. 2) into the digital signals and, after that, multiplexes them, thereby forming an input digital signal $D_{IN}$ and supplying to a buffer circuit 6. The buffer circuit 6 operates on the basis of address data and a clock signal which are generated from a buffer control circuit 8. That is, in the buffer control circuit 8, a reference signal which is output from a DSP (Digital Signal Processor) 12 is given to a reference signal forming circuit 14, thereby synchronizing the operations of the DSP 12 and buffer circuit 6.

The reference signal forming circuit 14 generates a clock signal to a read address data forming circuit 16 and a write address data forming circuit 18 on the basis of the reference signal. The read address data forming circuit 16 and write address data forming circuit 18 form read address data and write address data for buffer memory circuits 10A and 10B and a main buffer memory circuit 20, respectively, which are supplied to the buffer memory circuits 10A and 10B and main buffer memory circuit 20 through a selecting circuit 22, thereby switching the operations of the buffer memory circuits 10A and 10B and main buffer memory circuit 20 at a predetermined period.

The input digital signal $D_{IN}$ is accumulated into one of the buffer memory circuits 10A and 10B on the basis of the write address data which was formed by the write address data forming circuit 16 and supplied through the selecting circuit. When the input digital signal is fully accumulated into the one buffer memory circuit 10A or 10B, the input digital signal $D_{IN}$ which is subsequently supplied is then accumulated into the main buffer memory circuit 20. When the input digital signal $D_{IN}$ is fully accumulated into the main buffer memory circuit 20, the next input digital signal is then accumulated into the other buffer memory circuit 10B or 10A, respectively. For the above period of time, the input digital signal which was accumulated in the buffer memory circuit 10A or 10B and the input digital signal which was recorded in the main buffer memory are sequentially read out at a speed higher than that upon accumulation, and then supplied to the DSP 12. When the input digital signal is fully accumulated into the other buffer memory circuit 10B or 10A, the input digital signal which is subsequently supplied is again accumulated into the main buffer memory circuit 20. When the input digital signal is fully accumulated in the main buffer memory circuit 20, the next input digital signal is again accumulated into the one buffer memory circuit 10A or 10B. The above operations are sequentially repeated.

The DSP 12 is constructed by a signal processing circuit of a digital audio tape recorder. After the DSP 12 interleaves an input digital signal $D_{INN}$ which had been supplied from the buffer circuit 6, the DSP 12 adds an error detection/correction code and converts the resulting data into a recording signal $S_{REC}$ ((E) in FIG. 2) together with time information such as frame data or the like. Further, the DSP 12 outputs the produced recording signal $S_{REC}$ through an amplifying circuit 27, thereby recording the input signals $S_{IN}$ onto a magnetic tape 28 by a recording head 26 fixed on a rotary drum. A drive control circuit 30 intermittently drives the rotary drum and magnetic tape 28 synchronously with the timing of the recording signal $S_{REC}$, thereby intermittently obliquely recording the input digital signal $D_{INN}$ onto the magnetic tape 28. By converting the electrocardiogram signals $S_{IN}$ into the digital signal and recording, waveform distortion can be effectively avoided and the signals $S_{IN}$ can be recorded at a high accuracy.

Further, by accumulating the input digital signal $D_{IN}$ into the main buffer memory circuit 20 and intermittently recording, the electrocardiogram signal can be recorded for a long time. At this time, by intermittently outputting the recording signal $S_{REC}$ and intermittently driving the rotary drum and magnetic tape 28 synchronously with the recording signal $S_{REC}$, the electric power consumption can be reduced and the apparatus can be driven for a long time by a small battery. Therefore, the whole apparatus can be miniaturized by the decrease amount of such a small battery and the portability and using efficiency can be improved as compared with the conventional apparatus.

By actually intermittently driving the rotary drum and magnetic tape 28 as mentioned above, battery consumption can be extremely reduced because the electric power consumption which is required to drive the rotary drum and magnetic tape 28 is larger than the electric power consumption which is required in the circuitry from the input signal processor 4 to the amplifying circuit 27. That is, when it is now assumed that a ratio of the electric power consumption which is required for the circuitry from the input signal processor 4 to the amplifying circuit 27 and the electric power consumption which is required to drive the rotary drum and magnetic tape 28 is equal to 1:10, by intermittently driving the rotary drum and magnetic tape as mentioned above, almost all of the whole electric power consumption can be reduced to 1/10. On the other hand, if such a ratio is equal to 1:100 or 1:1000, the whole electric power consumption can be decreased to about 1/100 or 1/1000, respectively.

In the above construction, the electrocardiogram signals $S_{IN}$ which are generated from the four electrodes 2A to 2D are converted into the digital signals by the input signal processor 4 and, after that, they are multiplexed and converted into the input digital signal $D_{IN}$. The input digital signal $D_{IN}$ is accumulated into the buffer memory circuits 10A and 10B and main buffer memory circuit 2, as described above. The accumulated input digital signal $D_{INN}$ is supplied to the DSP 12 at a predetermined timing and interleaved by the DSP 12. After that, the error detection/correction code is added and the input digital signal is converted into the recording signal $S_{REC}$ together with the time information such as frame data or the like. The recording signal $S_{REC}$ is supplied to the magnetic head 26 fixed on the rotary drum through the amplifying circuit 27. The rotary drum and magnetic tape 28 are driven synchronously with the timing for the output, so that the recording signal is intermittently recorded onto the magnetic tape 28.

According to the above construction, the electrocardiogram signals $S_{IN}$ are converted into the digital signal and stored into the main buffer memory circuit 20 and, thereafter, the digital signal is intermittently recorded. Thus, the waveform distortion can be effectively avoided and the recording signal can be recorded at a high accuracy for a long time. Further, at this time, by intermittently driving the rotary drum and magnetic tape 28 synchronously with the recording signal $S_{REC}$, the electric power consumption can be reduced, the apparatus can be driven for a long time by a small battery, and the using efficiency can be improved.

The above embodiment has been described with respect to the case of intermittently driving the rotary drum and magnetic tape 28. However, the invention is not limited to such a case. For instance, the invention also can be widely applied in the case of intermittently driving the driving system such as where the running speed of the magnetic tape 28 is set to a value of 1/100 of the ordinary speed and only the rotary drum is intermittently driven or the like. Moreover, the above embodiment has been described with respect to the case of forming the recording signal by using the DSP of the digital audio tape recorder. However, the invention is not limited to such a case but can be also widely applied to other various cases using the DSP. Further, the above embodiment has been described with respect to the case where the electrocardiogram signals $S_{IN}$ which are generated from four electrodes 2A to 2D are recorded. However, the invention is not limited to such a case but can be also widely applied to the case of recording electrocardiogram signals which are generated from a plurality of electrodes or one electrode, the case of recording an electromyogram detected by an electromyograph, the case of recording brain waves, and the case of recording various measurement data for a long time.

FIG. 3 shows a block diagram of another embodiment according to the invention. In FIG. 3, the same parts and components as those shown in FIG. 1 are designated by the same reference numerals. In this another embodiment, analog signals which were generated from two electrodes 2A and 2B are supplied to A/D converters 9 and 11 through preamplifiers 3 and 5. The A/D converters 9 and 11 convert the analog signals into the digital signals at the timings of sampling pulses of 320 Hz which are supplied through a terminal 15 and supply the digital signals to a multiplexing circuit 7. In the multiplexing circuit 7, the digital signals supplied from the A/D converters 9 and 11 are sequentially selected by a time sharing manner and are supplied to the buffer memory 6. The digital signal which is generated from the multiplexing circuit 7 is stored into the buffer memory 6. The digital signal is read out by a control signal of 32 kHz which is supplied through a terminal 81 and is given to the DSP 12. A rate of the recording frequency and the reproducing frequency for the buffer memory 6 is equal to 1:100 (=320 Hz:32 kHz).

The analog signals generated from the electrodes 2A and 2B are the electric signals which are derived from a cardiac muscle when the heart beats. Almost all of the components of the analog signals are included in the frequency band until 100 Hz. Therefore, a low rate of about 1:100 (=320 Hz:32 kHz) can be sufficiently used as a rate between the recording and reproducing frequencies for the buffer memory 6.

Figure 4:
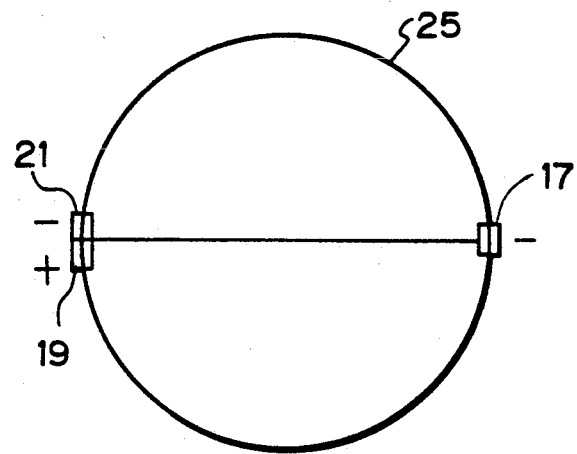
FIG. 4 is a diagram showing an arrangement of magnetic heads.

The recording signal generated from the DSP 12 is supplied to magnetic heads 17, 19, and 21 through recording amplifier 27 and recorded onto a magnetic tape T. FIG. 4 shows an arrangement of the magnetic heads 17, 19, and 21 of a rotary drum 25. That is, the magnetic head 17 and the magnetic heads 19 and 21 are attached to the rotary drum 25 so as to face at an angle of about 180°. A wrap angle of the magnetic tape T is set to 100°. The magnetic head 17 is used as a reproducing head.

Since the rate between the recording and reproducing frequencies of the digital signal for the buffer memory 6 is set to 1:100 (=320 Hz:32 kHz) as mentioned above, the DSP 12 and recording amplifier 27 execute signal processes for the digital signal which is read out only once for the hundred timings when the digital signal is stored into the buffer memory 6. Therefore, to reduce the electric power consumption, the DSP 12 and recording amplifier 27 are made operative only for a period of time corresponding to the above single timing to execute the signal processes and the recording signal is supplied to the magnetic heads 19 and 21. In the other period of time, the power supply is stopped and the circuit operation si stopped. Thus, low electric a power consumption can be realized. The rotation of the rotary drum 25 is continued even for the period of time when the operations of the DSP 12 and the recording amplifier 27 are stopped.

The above recording/reproducing rate relates to the tape feeding speed of the magnetic tape T. For instance, when it is now assumed that the magnetic tape is run at an extremely low speed of 1/100 of the ordinary feeding speed, the recording/reading rate is equal to 1/100 and it is sufficient that the necessary frequency band can be assured at such a rate. Therefore, the feeding speed of the magnetic tap T is set to the value of 1/100 of the ordinary tape feeding speed in correspondence to the recording/reading rate of 1:100 (=320 Hz:32 kHz) for the buffer memory 6. In the specification, the ordinary feeding speed denotes a feeding speed (55 mm/sec) when the audio signal is recorded. On the other hand, the feeding speed when an electrocardiogram waveform is recorded is set to 55 μm/sec, which is equal to 1/100 of the ordinary feeding speed.

The recording signal is supplied to the magnetic heads 19 and 21 only for a period of time corresponding to the timing to read out the digital signal from the buffer memory 6 and track TR are formed on the magnetic tape T. In the other period of time, no recording signal is supplied to the magnetic heads 19 and 21 and the track TR is not formed. Thus, the magnetic heads 19 and 21 merely scan on the magnetic tape T. The track TR can be formed to each of two upper and lower stages on the magnetic tape T. However, the embodiment is described with respect to the case of forming the track TR to the upper stage as an example.

Figure 5B:
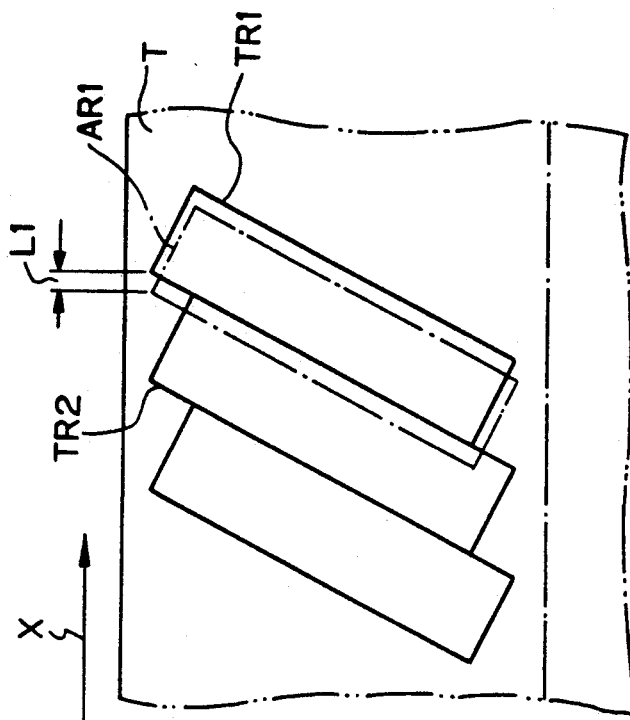
FIGS. 5A and 5B are diagrams for explaining the recording and reproduction for tracks.

As show in FIG. 5B, now assuming that the magnetic tape T is run in the direction of an arrow X at a speed of 1/100 of the ordinary tape feeding speed, the magnetic tape T is fed in the feeding direction (indicated by the arrow X) at a speed of 1/100 of the ordinary feeding speed for a period of time, for example, from a time after the magnetic head 19 formed a track $TR_1$ until a time when the magnetic head 21 reaches the magnetic tape T. Therefore, a region on the magnetic tape T which is scanned by the magnetic head 19 is a scanning area AR1 shown by an alternate long and short dash line in FIG. 5B. The scanning area AR1 by the magnetic head 21 is proportional to an angle interval between the magnetic heads 19 and 21 for the track TR1 and is deviated by only a length L1 of the tape corresponding to the speed of 1/100 of the ordinary feeding speed. The scanning operation is executed 99 times by the magnetic head 19 or 21 as mentioned above. A track TR2 is formed by the magnetic head 21 at a timing when the a magnetic head 21 executes the 101st scanning operation. Thus, the recording time which is 100 times as long as that in the case of recording at the ordinary feeding speed can be obtained.

In the example shown in the diagram, the electrodes 2A and 2B of two channels have been used. However, in the case of using four channels, a data amount is doubled. Accordingly, assuming that the tape feeding speed is not changed, the track width is reduced to ½ of the width specified by a format. Therefore, in such a case, the tape feeding speed is doubled, that is, the recording/reading rate is reduced to 1/50, thereby enabling one track TR to be formed by the fifty scanning operations.

In the reproducing mode, the recording signal is reproduced by the double density scan. The above reproducing mode will now be explained hereinbelow.

It is now assumed that, for instance, azimuth angles of the magnetic heads 21 and 17 are set to a − azimuth angle and an azimuth angle of the magnetic head 19 is set to a + azimuth angle. It is also assumed that tracks TRA1, TRA2, . . . on the magnetic tape T shown in FIG. 5A are formed by the magnetic head 19 and tracks TRB1, TRB2, . . . are formed by the magnetic head 21.

In the reproducing mode, the magnetic head 19 having a +azimuth angle and the magnetic head 17 having a − azimuth angle are used.

Figure 5A:
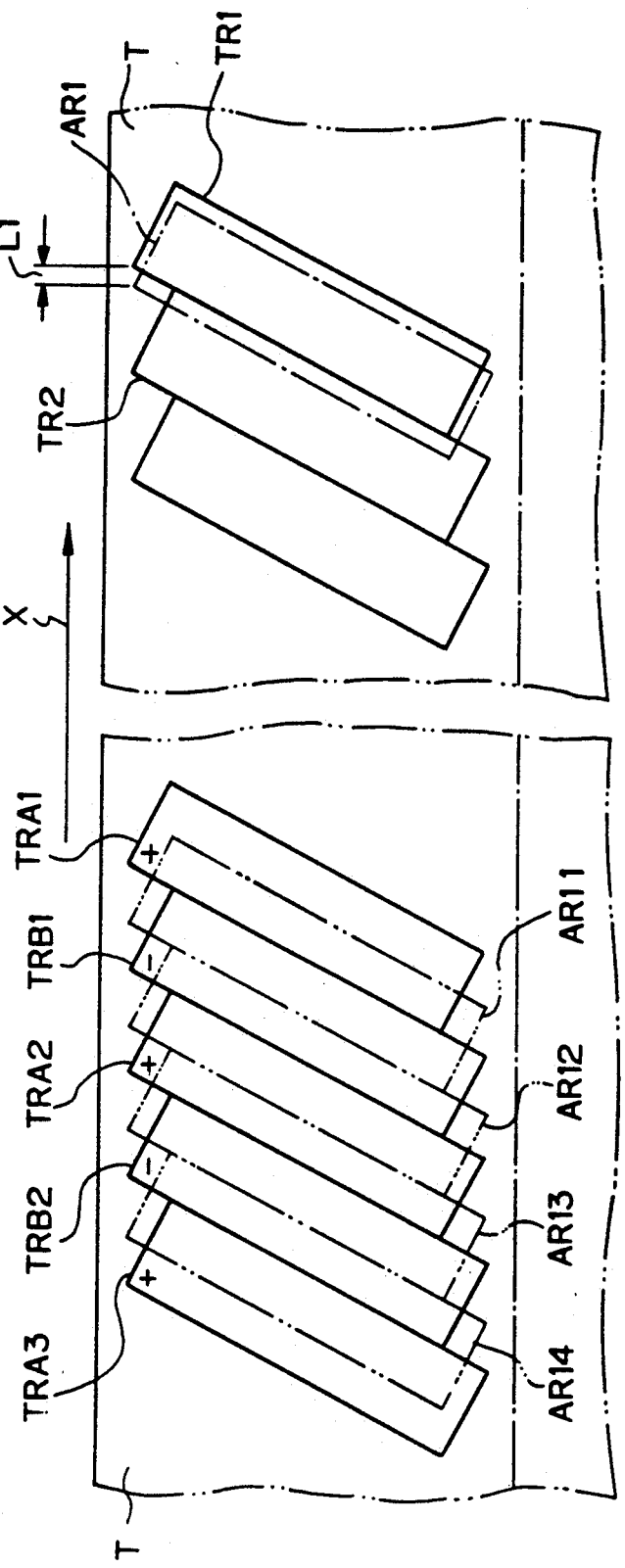

For example, there is a case where the tracks TRA1 to TRA3, TRB1, and TRB2 shown by solid lines in FIG. 5A are scanned by the magnetic head 19 and the tracks TRA1 to TRA3, TRB1, and TRB2 are overlappingly scanned by the magnetic head 17 as shown by broken lines AR11 to AR14 in FIG. 5A.

The recording signals are reproduced from the tracks TRA1, TRA2, and TRA3 having the same azimuth angle by the scanning operation of the magnetic head 19, while no recording signal is reproduced from the tracks TRB1 and TRB2 having the azimuth angle opposite to the above azimuth angle. On the other hand, the recording signals are reproduced from the tracks TRB1 and TRB2 having the same azimuth angle by the two scanning operations by the magnetic head 17. No recording signal is reproduced from the tracks TRA1, TRA2, and TRA3 having the azimuth angle opposite to the above azimuth angle. In this case, although the scanning timings of the magnetic head 17 for the tracks TRB1 and TRB2 differ, the recording signals can be reproduced from the tracks TRB1 and TRB2 by using a memory.

Thus, the recording signals can be reproduced from all of the tracks TRA1 to TRA3, . . ., TRB1, TRB2, . . . . In the reproducing mode, it is sufficient to scan the tracks TRA1 to TRA3, . . ., TRB1, TRB2, . . . at an ordinary reproducing speed. In this case, the reproducing time can be reduced to 1/100 of the time which was required for recording. For example, assuming that the digital signal of the electrocardiogram waveforms of 24 hours has been recorded, the time which is required for reproduction is equal to a (24/100) hours, that is, 14.4 minutes.

The digital signal of the electrocardiogram waveform is decoded and analyzed by a computer. When the tape is fed, a motive power which is formed by reducing a rotational force from a drum motor through gears is used. The relation with the rotary drum 25 is accomplished by simple and certain means. However, an accurate servo control system can be also constructed by using two motors.

A tape recorder and a tape cassette which can be applied to the embodiment of the invention will now be described hereinbelow.

The tape recorder converts the analog signal into the digital signal and records to a micro tape cassette. The digital signal which is recorded doesn't satisfy the standard of the conventional digital audio tape recorder which is what is called a DAT.

The above digital recording and reproducing apparatus mainly has the following two features.

I. Since the apparatus has a structure in which the rotary drum is inserted into the tape cassette in the recording/reproducing mode, the micro tape cassette (for instance, $30 \times 21.5 \times 5$ mm$^3$) different from the standard of the conventional DAT is realized. II. Since the double signal reading/double density scanning method is used in the reproducing mode, even if a tracking error occurred upon reproduction or even if the accurate tracking control as in the conventional DAT is not performed, data can be accurately reproduced so long as the data is correctly rearranged because all of the data are read out from the recorded tracks.

The above feature I will now be described hereinbelow.

Figure 6:
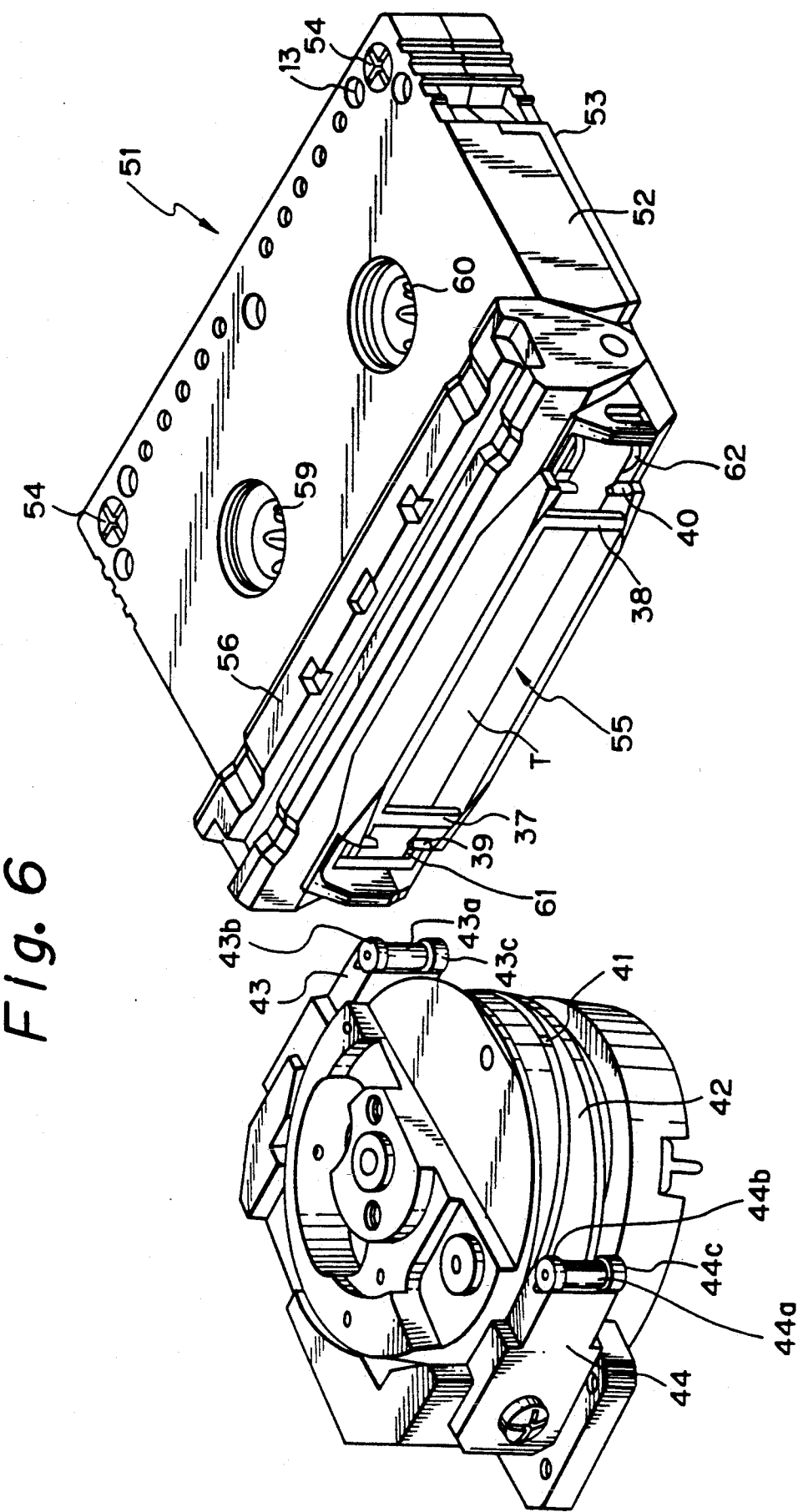
FIGS. 6 to 11 are diagrams for explaining a tape recorder and a tape cassette which can be applied to the invention.

As shown in FIG. 6, a tape cassette 51 is formed by arranging an upper half 52 and a lower half 53 so as to face each other and clamping with screws 54. An opening portion 55 is formed on the front surface side of both halves 52 and 53. When the tape cassette 51 is loaded into the digital recording and reproducing apparatus, a lid 56 is rotated upwardly or downwardly, so that the opening portion 55 is opened.

The magnetic tape T is enclosed between the upper and lower halves 52 and 53 in a wrapped state between a pair of both hubs 57 and 58 which are arranged in correspondence to through holes 59 and 60 of hub drive shafts. The magnetic tape T is taken out to the opening portion 55 in a suspending state through pinch rollers 61 and 62 serving as guide rollers which are rotatably axially supported to both sides of the opening portion 55.

For the magnetic tape T which is enclosed in the tape cassette 51, a signal is recorded and/or reproduced by a magnetic head 41 by the helical scan method. In the digital recording and reproducing apparatus, in order to enable the magnetic tape T to be certainly helically come into slide contact with the rotary drum 42, tape guide members in the tape cassette 51 have functions of a vertical guide and an oblique pin in the ordinary tape loading mechanism.

Figure 7:
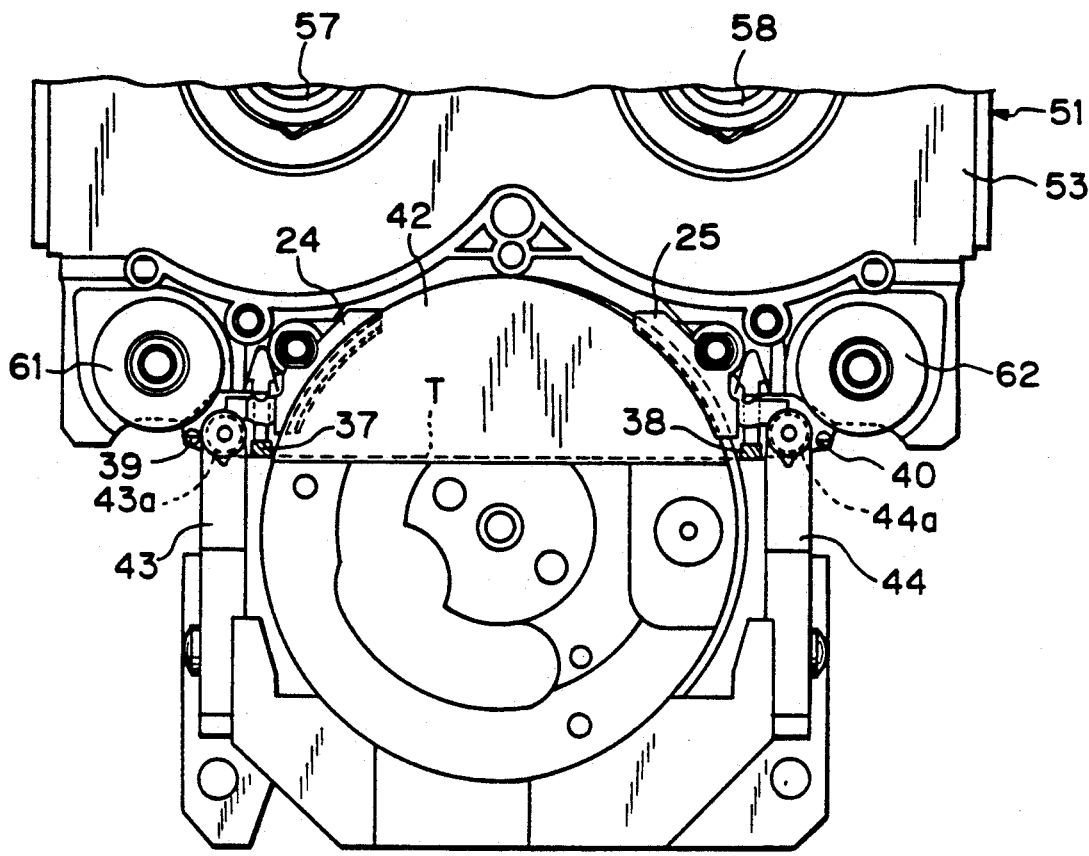

As shown in FIG. 7, tape guide members 24 and 25 are provided between the pinch rollers 61 and 62 in the inserting portion of the rotary drum 42 in the opening portion 55 of the tape cassette 51. The tape guide members 24 and 25 are arranged so as to swing and be movable in the lateral direction in a state in which the tape guide members 24 and 25 face each other.

Wing guides 43 and 44 are provided in both side portions of a rotary drum 42. Rollers 43a and 44a are attached to the front edge portions of the wing guides 43 and 44.

Figure 8:
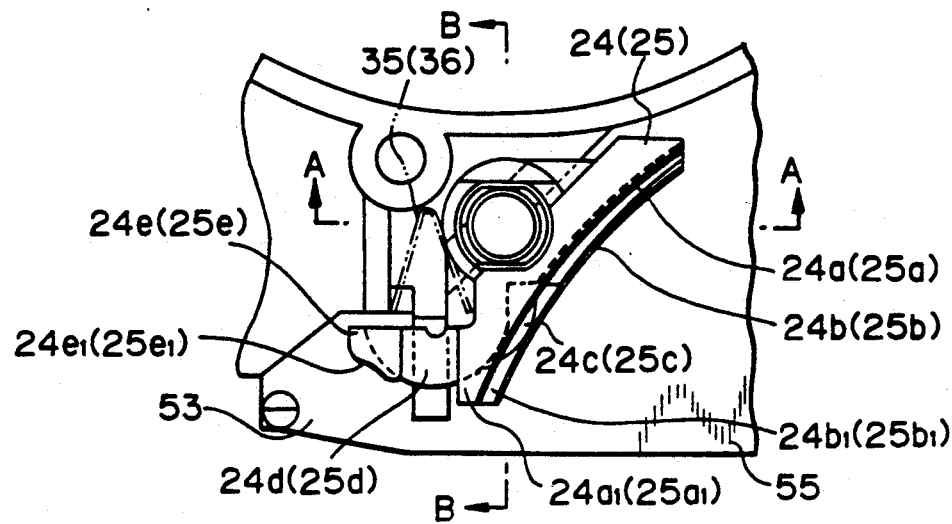
Figure 9:
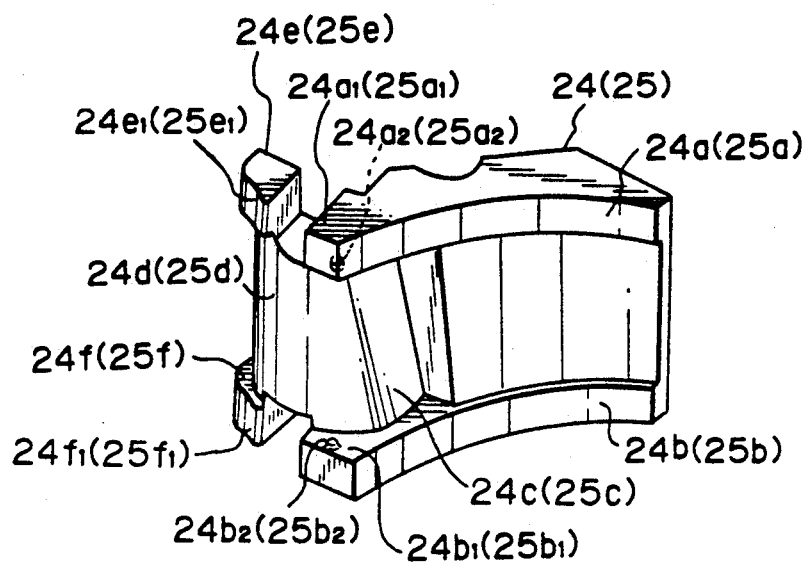
Figure 10:
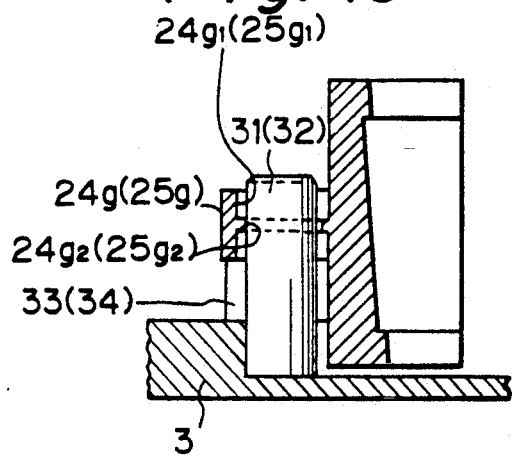
Figure 11:
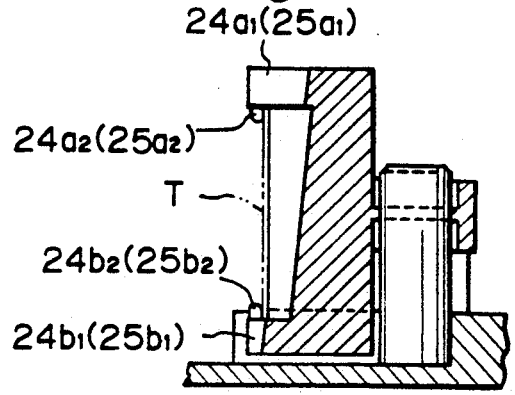

As shown in FIGS. 8 to 10, the tape guide members 24 and 25 are formed as inclined surfaces whose inner surface sides have a curved arc shape whose diameter is slightly smaller than a diameter of rotary drum 42 and are set in the mutually opposite directions with respect to the vertical direction. Projection-shaped supporting edge portions (24a and 24b) and (25a and 25b) are formed in the upper and lower portions of the inclined inner surfaces at intervals each of which is slightly wider than a width of magnetic tape T. The regions between the upper and lower supporting edge portions are used as inclined guide surfaces 24c and 25c. The regions on the front surface side which continue with the inclined guide surfaces 24c and 25c are used as vertical cylindrical guide surfaces 24d and 25d.

Bearing brackets 24g and 25g are projected onto the tape guide members 24 and 25 so as to be located on the outer surface sides of the guide surfaces 24c and 25c. Shaft holes 24g1 and 25g1 of the bearing brackets are formed as holes which are laterally long. Projecting shaft supporting edges 24g2 and 25g2 are formed on the inner peripheral surfaces of the shaft holes 24g1 and 25g1 so as to be located at almost central positions.

For the tape guide members 24 and 25 with the above structure, the bearing brackets 24g and 25g are inserted to shafts 31 and 32 formed vertically on the lower half 53 and the lower surface sides of the bearing brackets are put onto mounting members 33 and 34.

The upper surface sides of the tape guide members 24 and 25 are away from the inner surface of the upper half 52 by pressing members (not shown) formed on the inner surface of the upper half 52.

Thus, the tape guide members 24 and 25 are supported in a state in which they are floating from the inside surfaces of the upper and lower halves 52 and 53 at a desired interval and are rotatable with respect to the shafts 31 and 32. The tape guide members can obliquely move, namely, swing in the lateral direction by using contacts between the projecting shaft supporting edges 24g2 and 25g2 and the shafts 31 and 32 as fulcrums and can move in the lateral direction between the shaft holes 24g1 and 25g1.

On the other hand, the tape guide members 24 and 25 are deviated in the central direction of the opening portion 55 by springs 35 and 36.

When the tape cassette 51 is loaded into the digital recording and reproducing apparatus, the opening portion 55 is opened and the rotary drum 42 is inserted into the opening portion 55 integratedly with both of the wing guides 43 and 44 in a slide contact state with the magnetic tape T. The front edge portions of the wing guides 43 and 44 are also inserted into the gaps between supporting members 37 and 38 and guide projections 39 and 40.

In the opening portion 55, the rotary drum 42 is come into contact with the supporting edge portions 24a, 24b, 25a, and 25b of the tape guide members 24 and 25 which are held in a state in which they can swing and are movable in the lateral direction, that is, they are substantially freely movable.

Upon contacting, both of the tape guide members 24 and 25 are certainly come into contact with the peripheral surface of the rotary drum 42 irrespective of the positions of the tape guide members 24 and 25 due to the rotation using the shaft supporting portions by the shafts 31 and 32 as centers or the inclining motions using the contact portions of the projecting shaft supporting edges 24g2 and 25g2 of the bearing brackets 24g and 25g to the shafts 31 and 32 as fulcrums.

On the other hand, when the rollers 43a and 44a are inserted into the gaps between the supporting members 37 and 38 and the guide projections 39 and 40, the rollers are come into rolling contact with the magnetic tape T. Flanges (43b and 43c) and (44b and 44c) which axially support the rollers 43a and 44a are come into contact with pressing edge portions 24e, 24f, 25e, and 25f of the tape guide members 24 and 25 and abut on concave portions 24e1, 24f1, 25e1, and 25f1 of the pressing edge portions. Thus, the tape guide members 24 and 25 are held in a parallel state in the front/back directions with respect to the rotary drum 42.

On the other hand, the magnetic tape T which is rove between the pinch rollers 61 and 62 is located between receiving edge portions 24a1, 24b1, 25a1, and 25b1 of the tape guide members 24 and 25 from the beginning and is enclosed in a state in which the positions are restricted by engaging projections (24a2 and 24b2) and (25a2 and 25b2), respectively. Therefore, when the rotary drum 42 is inserted into the opening portion 55, the magnetic tape T is certainly slided along the inclined guide surfaces 24c and 25c of the tape guide members 24 and 25.

In such a state, the magnetic tape T is come into slide contact with the vertical cylindrical guide surfaces 24d and 25d and the inclined guide surfaces 24c and 25c between the tape guide members 24 and 25. Thus, the magnetic tape is set to a position of an ideal tape path for the rotary drum 42 and is run.

The main specifications of the digital recording and reproducing apparatus are as follows.

The dimensions are set to, for example, $115 \times 50 \times 21$ mm$^3$ and the apparatus is extremely miniaturized.

For instance, assuming that the tape width (2.5 mm) is vertically divided into two portions and the signal is reciprocatingly recorded, the recording or reproducing time is equal to two hours by the reciprocating operations (one hour for one way). The total recording capacity is set to 790 Mbytes. The fast forward feeding time is set to about three minutes. The recording or reproduction of five hours can be performed by using one alkaline battery of the UM3 type.

Stereophonic audio signals can be realized because audio signals of two right and left channels can be recorded.

The drum diameter is set to 14.8 mm. The wrap angle of the tape is set to 100° in a state in which the recording/reproducing heads are arranged so as to face each other at an angle of 180°. A metal tape of the evaporation deposition type is used.

In the embodiment, the sampling frequency of the A/D converters 9 and 11 is set to 320 Hz. However, it can be also set to 640 Hz as necessary. The frequency of the control signal to read out the digital signal from the buffer memory 6 is set to 32 kHz. However, the invention is not limited to such a value and can also use 64 kHz. The tape feeding speed can be also changed in correspondence to a change in sampling frequency and a change in frequency of the control signal mentioned above.

Although the above embodiment has been described with respect to the case of the electrodes 2A and 2B of two channels as an example, the invention is not limited to such a case. A number of electrodes can be also used as necessary.

Although the embodiment has been described with respect to the electrocardiogram waveform as an example of the analog signal, the invention is not limited to such a case. The invention can be also applied to other organism signals of a narrow band and a low frequency such as electromyogram waveform, brain wave, and the like.

Figure 12:
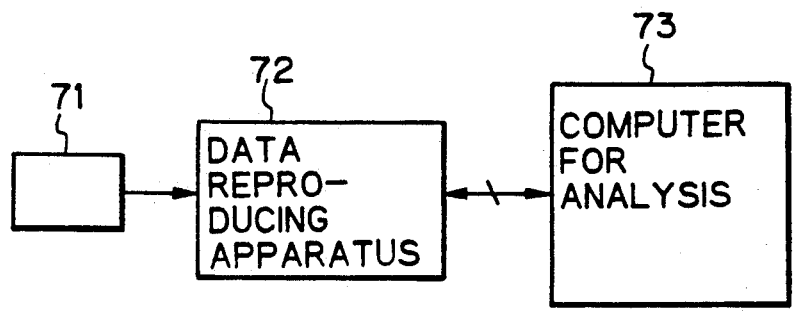
FIG. 12 is a block diagram of a main section of an automatic analyzing system which can be applied to the invention.

FIG. 12 shows a block diagram of the main section of an automatic analyzing system of the electrocardiogram waveforms which were recorded as mentioned above.

When a micro tape cassette 71 on which the electrocardiogram waveforms were magnetically recorded as digital modulation signals is loaded into a data reproducing apparatus 72, the digital modulation signal of the electrocardiogram waveform recorded on a magnetic tape (not shown) is reproduced by the magnetic heads. The data reproducing apparatus 72 has a DSP. The DSP demodulates the original digital signal from the reproduced digital modulation signal and, thereafter, executes signal processes such as filtering, error correction, deinterleave, and the like to the demodulated original digital signal. Thus, the digital data of the electrocardiogram waveform is reproduced and supplied to a computer 73 for analysis. The computer 73 classifies the morphology of the electrocardiogram waveform in accordance with a flowchart shown in FIG. 13.

FIG. 13 shows the flowchart for classification of the morphology of an electrocardiogram waveform of an arrhythmia. Noises are eliminated in step 101. This is because since electrocardiogram waveforms are recorded for a long time, noises due to the motions in a daily life such as walking, lying on one's side, etc. are mixed, so that it is difficult to execute the automatic analysis in such a state. Then, step 102 follows.

Figure 14:
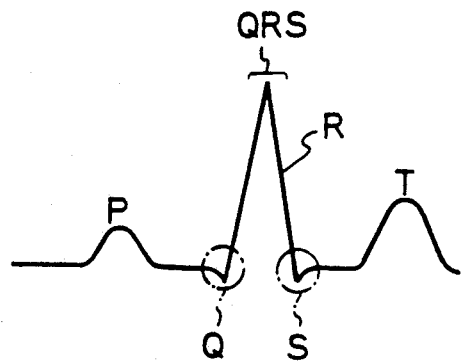
FIG. 14 is a waveform diagram showing an electrocardiogram waveform in a period of one heartbeat.

In step 102, a QRS waveform is extracted by a peak detection. FIG. 14 shows an electrocardiogram waveform of one heartbeat comprising: a P wave P, a QRS waveform QRS consisting of a Q wave Q, an R wave R, and an S wave S; and a T wave T. In the diagram, the QRS waveform QRS is extracted by the peak detection. Then, step 103 follows.

In step 103, characteristics of the extracted QRS waveform QRS, for instance, a width, a height, and the like are extracted. The presence or absence of abnormality, that is, whether an arrhythmia has appeared or not is discriminated by comparing the extracted characteristics with the characteristics of the normal QRS waveform. If the existence of the arrhythmia has been determined, step 104 follows. If the absence of the arrhythmia has been decided, the processing routine is finished.

Figure 15:
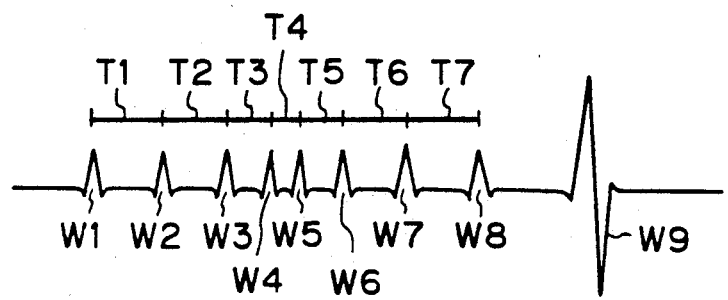

In step 104, a check is made to see if the arrhythmia relates to a morphology abnormality or a rhythm abnormality of the QRS waveform QRS or relates to only a rhythm abnormality. For instance, assuming that electrocardiogram waveforms as shown in FIG. 15 were time sequentially obtained, waveforms W1 to W8 have substantially the same shape. However, there is a fluctuation among periods T1 to T7 of the vertexes of the waveforms W1 to W8, so that the occurrence of the rhythm abnormality is determined. On the other hand, an amplitude and a shape of waveform W9 largely differ from those of the other waveforms W1 to W8, so that the occurrence of the morphology abnormality is decided. Although not shown, there is also a waveform of the type in which both of the rhythm abnormality and the morphology abnormality overlap.

In the case of only the rhythm abnormality, the processing routine advances to step 105 and the rhythm abnormality is analyzed. In the analysis of the rhythm abnormality, as in the case of the waveforms W1 to W8 shown in FIG. 15, a check is made to see if an abnormality exists in the periods among the vertexes of the R waves R of the QRS waveforms QRS or not. If such an abnormality occurred, a degree of abnormality of the periods among the vertexes of the R waves R is calculated. Then, the processing routine is finished.

In the other two cases, that is, in the case of the morphology abnormality or the case where both of the morphology abnormality and the rhythm abnormality overlap, step 106 follows. The rhythm abnormality in this case is ignored. In step 106, a similarity is calculated among the electrocardiogram waveforms which are time sequentially obtained. The similarity calculation is executed by the following equation, by which a similarity SI is obtained.

$$SI = \frac{\sum_{i=1}^{N} x_i \cdot y_i}{\sqrt{\sum_{i=1}^{N} (x_i)^2} \sqrt{\sum_{i=1}^{N} (y_i)^2}}$$

Figure 16:
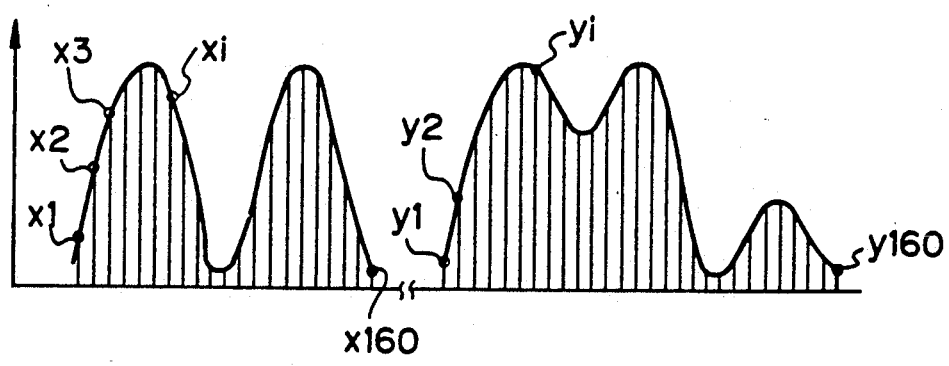
FIGS. 15 to 17 are diagrams for explaining similarity calculations.

In the above equation, $x_i$ denotes a value which is obtained when the QRS waveform QRS of one electrocardiogram waveform in the electrocardiogram waveforms which had been determined to be a morphology abnormality and registered was sampled every 500 msec as shown in FIG. 16. N denotes the number of sampling points (for example, N=160). $y_i$ denotes a value which is obtained when the QRS waveform QRS which had newly been detected as a morphology abnormality was sampled every 500 msec as shown in FIG. 16. N indicates the number of sampling points (e.g., N=160).

In the above similarity calculation, a smoothing differentiation is executed to the electrocardiogram waveform in order to prevent influences by the noises, a base line fluctuation, and the like. After the similarity SI was obtained, step 107 follows. In step 107, a degree of the similarity SI is compared with a predetermined reference value (for example, 0.9). That is, if (0.9≦SI), it is determined that the extracted electrocardiogram waveform is the same as either one of the electrocardiogram waveforms which have already been determined as a morphology abnormality by the above similarity calculation and registered. In the next step 108, the electrocardiogram waveform is classified into an electrocardiogram waveform similar to either one of the registered electrocardiogram waveforms. An appearance frequency of the classified electrocardiogram waveform is counted. If (0.9>SI), the extracted electrocardiogram waveform is newly registered as a QRS waveform QRS of a new morphology abnormality in step 109.

Figure 17:
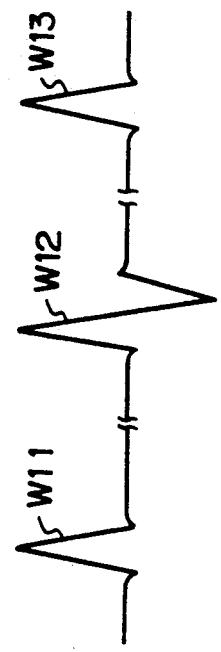

For example, assuming that an electrocardiogram waveform W11 shown in FIG. 17 has already been registered as a morphology abnormality, a morphology of electrocardiogram waveform W12 which is subsequently obtained largely differs from that of the electrocardiogram waveform W11 which has already been registered, so that it is determined that the similarity SI<0.9. Thus, the electrocardiogram waveform W12 is newly registered as an electrocardiogram waveform of a morphology abnormality. A morphology of next electrocardiogram waveform W13 is similar to that of the electrocardiogram waveform W11, so that it is decided that the similarity SI>0.9 as compared with the electrocardiogram waveform W11. On the other hand, the morphology of the electrocardiogram waveform W13 largely differs from that of the electrocardiogram waveform W12, so that it is determined that the similarity SI<0.9 as compared with the electrocardiogram waveform W12. Therefore, it is determined that the electrocardiogram waveform W13 has the same morphology as that of the electrocardiogram waveform W11. The appearance frequency of the electrocardiogram waveform W11 is counted up.

The processing routine is finished in step 109. The above processing steps are repeatedly executed with respect to all of the electrocardiogram waveforms.

In the embodiment, since the morphology of the electrocardiogram waveform is classified on the basis of the similarity SI, the morphology of the waveform can be classified by the clear reference. The morphology of the QRS waveform QRS which was determined to be an abnormality and the appearance frequency and period of the electrocardiogram waveform of each morphology can be obtained. Thus, the classification accuracy of the electrocardiogram waveform can be improved.

The present invention is not limited to the foregoing embodiments but many modifications and variations are possible within the spirit and scope of the appended claims of the invention.

What is claimed is:

1. A magnetic recording apparatus comprising:
a signal processor configured for processing an analog signal to produce a digital signal comprising a serial stream of digital data;
memory means having parallel first, second and third memories connected to said signal processor and configured for storing therein at a first rate serial stream of digital data in accordance with the following repeating order; said first memory, said second memory, said third memory and then said second memory, and for retrieving therefrom at a second rate higher than said first rate the serial stream of digital data from the appropriate memory during the storage of said serial stream of digital data into another of said memories;
recording signal generating means for converting the serial stream of digital data retrieved from the memory means to a recording signal suitable for recording;
recording means for recording the recording signal; and
drive means for driving said recording means intermittently in response to a timing signal and configured for outputting the recording signal from the recording signal generating means to the recording means.

2. The magnetic recording apparatus of claim 1 further comprising:
a magnetic tape and tape drive therefor, which tape drive drives said tape at a speed which is a function of a ratio of said first rate and said second rate.

3. A magnetic recording apparatus comprising:
a signal processor configured for processing an analog signal so as to produce a digital signal comprising a serial stream of digital data;
memory means for storing said serial stream of digital signal at a first frequency and retrieving the serial stream of digital signal at a second frequency higher than said first frequency; and
recording means for recording the digital signal which is retrieved from the memory means to a magnetic tape which is moving at a speed determined by a ratio of said first and second frequencies.

* * * * *